United States Patent [19]

Hou et al.

[11] Patent Number: 4,948,885
[45] Date of Patent: Aug. 14, 1990

[54] SYNTHESIS OF AZETIDINONES

[75] Inventors: Donald Hou, Verona; Yee-Shing Wong, Clifton; Dinesh Gala, East Brunswick; Martin Steinman, Livingston, all of N.J.

[73] Assignee: Schering-Plough Corp., Kenilworth, N.J.

[21] Appl. No.: 370,520

[22] Filed: Jun. 23, 1989

Related U.S. Application Data

[62] Division of Ser. No. 203,385, Jun. 7, 1988, Pat. No. 4,876,338, which is a division of Ser. No. 887,394, Jul. 21, 1986, Pat. No. 4,767,853.

[51] Int. Cl.$^5$ .................. C07D 403/12; C07D 205/09; C07F 7/18
[52] U.S. Cl. .................................................. 540/358
[58] Field of Search ......................................... 540/358

[56] References Cited

U.S. PATENT DOCUMENTS

| | | | |
|---|---|---|---|
| 3,311,638 | 3/1967 | Wolfe | 260/306.7 |
| 3,948,927 | 4/1976 | Wolfe | 260/307 FA |
| 4,411,906 | 10/1983 | Girijavallabhan | 424/270 |
| 4,431,658 | 2/1984 | Afonso | 260/245.3 |
| 4,435,412 | 3/1984 | Girijavallabhan | 260/239 A |
| 4,435,413 | 3/1984 | Girijavallabhan | 424/270 |
| 4,437,183 | 8/1982 | Afonso | 424/270 |
| 4,443,373 | 4/1984 | Girijavallabhan et al. | 260/245.2 R |
| 4,456,609 | 6/1984 | McCombie | 424/270 |
| 4,503,064 | 3/1985 | Girijavallabhan et al. | 514/210 |
| 4,530,793 | 7/1985 | Girijavallabhan et al. | 260/245.2 R |
| 4,559,333 | 12/1985 | Girijavallabhan et al. | 514/192 |
| 4,584,133 | 4/1986 | Girijavallabhan | 260/239 A |
| 4,596,677 | 6/1986 | Martel et al. | 260/245.2 R |
| 4,610,823 | 9/1986 | DiNinno | 540/350 |
| 4,675,317 | 6/1987 | DiNinno | 540/310 |

OTHER PUBLICATIONS

Gala, J. Org. Chem. 51, 4488 (1986).
DiNinno et al., Tetrahedron Letters, 23, 3535–3538 (1982).
Wolfe et al., Can. J. Chem. 53, 497–512 (1975).
DiNinno et al., J. Org. Chem. 42, 2960–2965 (1977).

*Primary Examiner*—Mark L. Berch
*Attorney, Agent, or Firm*—Gerald S. Rosen; Stephen I. Miller

[57] ABSTRACT

There is disclosed a compound represented by the formula

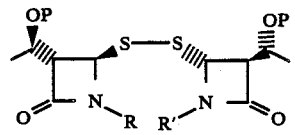

wherein each P is hydrogen or a hydroxy protecting group and R and R' are each the same and are hydrogen,

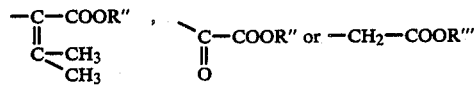

wherein R" is lower alkyl and R'" is a carboxy protecting group.

The compounds are useful as intermediates for preparing penems.

3 Claims, No Drawings

SYNTHESIS OF AZETIDINONES

This is a division of application Ser. No. 203,385, field June 7, 1988 U.S. Pat. No. 4,876,338 which is a division of application Ser. No. 887,394, filed 7/21/86 now U.S Pat. No. 4,767,853.

BACKGROUND

This invention relates to an improvement in a multi-step stereospecific process for producing azetidinones which are useful as intermediates for preparing penems. More particularly this invention relates to an improvement in the stereospecific multi-step process in which anhydropenicillin, i.e., (5R,6S,8R)-3,7-dioxo-6-(1-hydroxyethyl)-2-(1-methylethylidene)-4-thia-1-azabicyclo[3.2 0]heptane, is converted to (3S,4R,5R)-1-(allyloxycarbonyl)methyl-3-(1-hydroxyethyl)-4-beta-naphthoxythiocarbonylthio-2-azetidinone or its hydroxy protected analog.

In commonly assigned pending U.S. patent application Ser. No. 775,975, filed Sept. 13, 1985, now abandoned the preparation of anhydropenicillin, designated as compound 1, is disclosed on pages 8–10 inclusive, which pages are incorporated by reference herein. The conversion of compound 1 to the hydroxy protected analog is disclosed in U.S. patent application Ser. No. 775,975, filed Sept. 13, 1985, abandoned on page 14 last paragraph and page 15, first paragraph, which paragraphs are incorporated by reference herein.

The anhydropenicillin is converted to azetidinones useful as intermediates for making penems by a multi-step process.

The process of this invention does not require the removal and re-introduction of the sulfur atom which originates with 6-APA, the compound used to make anhydropenicillin (depicted below as compound 1). In addition, the process does not require the isolation of all the intermediates and is thus efficient and economical. The process utilizes and provides a means to prepare novel and known intermediates used ultimately in known processes for making penems.

Nomenclature used herein for the various penem and azetidinone compounds is illustrated as follows, with the appropriate numbering system indicated and the stereoisomerism shown.

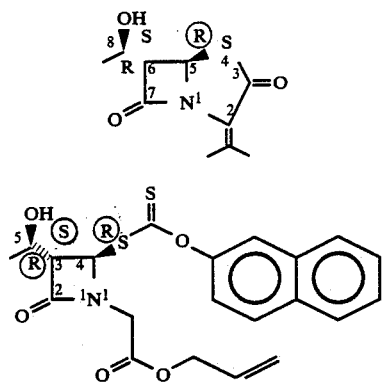

(5R,6S,8R)-3,7-dioxo-6-(1-hydroxyethyl)-2-(1-methylethylidene)-4-thia-1-azabicyclo[3.2.0 ]heptane refers to compound 1; and (3S,4R,5R)-1-(allyloxycarbonyl)-methyl-3-(1-hydroxyethyl)-4-betanaphthoxythiocarbonylthio-2-azetidinone refers to compound N'.

The preferred stereochemistry of the 1-hydroxyethyl side chain on compounds used in and prepared by the process of this invention is R as defined by the Cahn-Ingold-Prelog rules, as indicated by the R below carbon 5 in compound N' and carbon 8 in compound 1 and the remaining chiral centers are indicated by the appropriate R and S.

SUMMARY OF THE INVENTION

This invention provides an improved and novel stereospecific process for converting (5R,6S,8R)-3,7-dioxo-6-(1-hydroxyethyl)-2-(1-methylethylidene)-4-thia-1-azabicyclo[3 2 0]heptane into azetidinones useful in multi-step processes for producing penems. Penems are a known group of antibacterial compounds. More particularly, this invention provides the means to produce azetidinones represented by the following formula N

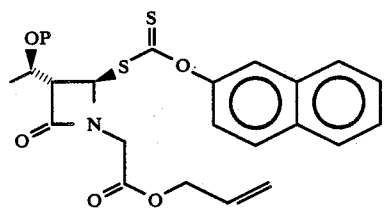

wherein P is hydrogen or a hydroxy protecting group; from a compound represented by the following formula 1

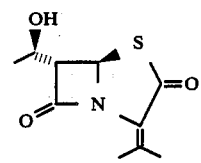

by protecting the hydroxy group with a readily removable hydroxy protecting group, then converting the resulting compound by ozonolysis followed by reaction with a trialkyl phosphite then hydrolysis into a compound represented by the following formula 5

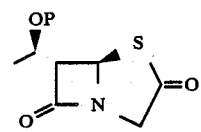

wherein P is a hydroxy protecting group.

Compound 5 is then converted to compound N' wherein P is hydrogen by reaction with allyl alcohol and HCl followed by reaction with O-2-naphthalenyl-carbonochloridothioate, or compound 5 can be converted to compound N wherein P is a hydroxy protecting group i.e. compound N''', preferably t-butyldimethylsilyl, by reaction with silver imidazolate and allyl alcohol followed by reaction with O-2-naphthalenyl-carbonochloridothioate. Compound N and its use in processes for preparing penems is disclosed in, e.g., U.S. Pat. Nos. 4,503,064; 4,530,793 4,559,333 and 4,584,133.

In another aspect, this invention provides an improved stereospecific process for converting compound 1 into compound N' by first making the hydroxy protected analog of compound 1, heating it with oxygen and cuprous chloride, then reacting the resulting diazetidinone with ozone followed by ammonium hydroxide, then allyliodoacetate. The protecting group on the hydroxyl group of the resulting product is removed with acid and the disulfide bond is broken by means of zinc and acid. The resulting unisolated compound is then treated with O-2-naphthalenylcarbonochloridothioate to make compound N'.

Novel compounds produced and used in this invention and which are a part thereof are compound 5 and the dimers of the following formula M

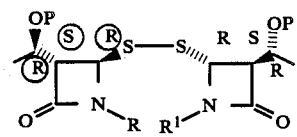

wherein P is hydrogen or a hydroxy protecting group and R and R¹ are the same and are either

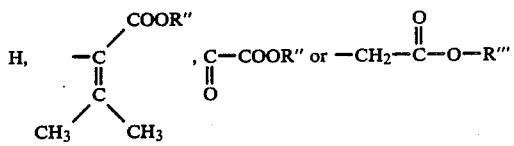

wherein R" is lower alkyl, preferably methyl, and R''' is a carboxy protecting group, preferably allyl.

DETAILED DESCRIPTION

In one aspect, the process of this invention comprises converting anhydropenicillin to a compound represented by formula N according to the following reaction Scheme A. The preferred stereoisomers are depicted for illustrative purposes in all reaction schemes which follow. Although the preferred stereochemistry of the reactants and intermediates in the process of this invention is as indicated in the various depicted structural formulas, it is to be understood that the process of this invention is operative for other stereoisomers and involves merely the selection of reactants having the desired stereochemical configuration and reaction conditions which result in the desired stereoisomers.

REACTION SCHEME A

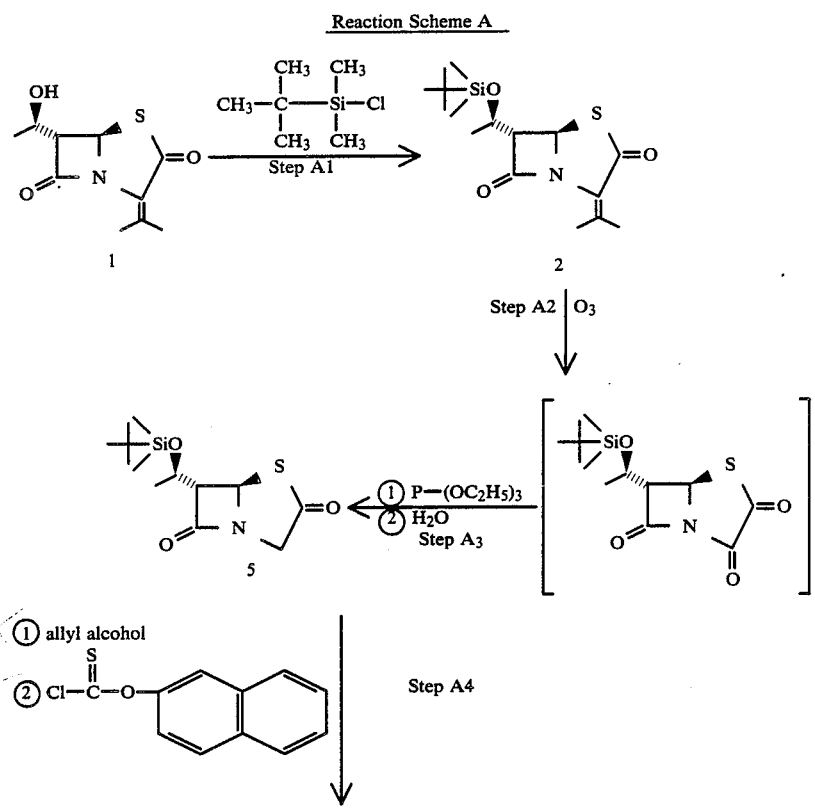

Reaction Scheme A

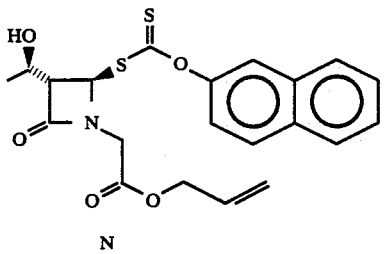

In Step A1 of Reaction Scheme A, the hydroxy group of compound 1 is protected by reaction of compound 1 in an organic base, e.g. triethylamine, and a suitable inert organic solvent, e.g., methylene chloride, under a dry, inert atmosphere, e.g., nitrogen, with a silylating agent, e.g., tertiary butyldimethylsilyl chloride or tertiary butyldimethylsilyltriflate in dimethylformamide (DMF) or in pyridine with a catalytic amount of 4-N,N-dimethylaminopyridine or without the catalyst to produce compound 2.

In Step A2, compound 2 in an anhydrous inert, organic solvent, e.g., dry acetone, is treated with ozone at about −50° to −85° C. preferably about −78° C. under an inert atmosphere, e.g. nitrogen, until the reaction is complete as evidenced by the formation of a blue colored reaction solution. The resulting compound 3 is not isolated but is used in the next step of the reaction, Step A3.

In Step A3, compound 3 from Step A2 is treated with a triloweralkylphosphite, preferably triethylphosphite, and allowed to warm to room temperature (about 20°–25° C.). The reaction mixture is then treated with water until the reaction is complete, about 30 minutes, and the product, compound 5, is recovered as a white solid.

In Step A4, compound 5 is converted to compound N wherein P is hydrogen, in a two step reaction, first, by reaction with allyl alcohol in concentrated hydrochloric acid at room temperature until the reaction is complete, e g. about 30 hours, and second, by reaction of the resulting product in an inert organic solvent, e.g. methylene chloride, at about −10° C. to +10° C., preferably 0° C., with O-2-naththalenylcarbonochloridothioate, with or without an organic nitrogen base, then recovering the product, compound N wherein P is hydrogen.

Compound 5 can also, in a more preferred embodiment, be converted to compound N wherein P is a hydroxy protecting group, according to the following Reaction Scheme B.

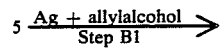

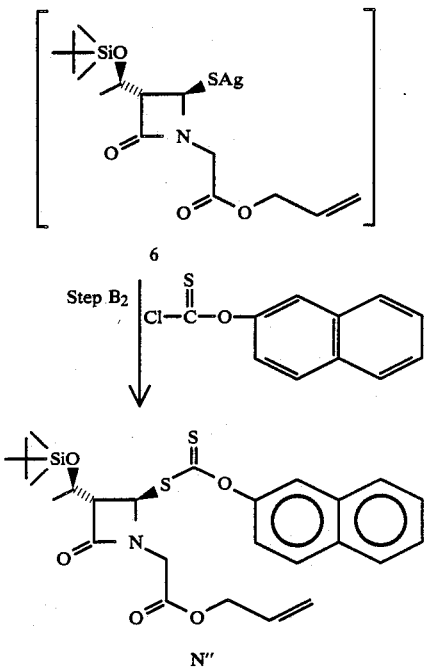

In Step B1 of Reaction Scheme B, the penem ring of compound 5 is opened by reaction with allyl alcohol and silver imidazolate at room temperature until the reaction is completed in about 30 hours. The resulting product, compound 6, need not be isolated for use in the following Step B2.

In Step B2, compound 6 is converted to compound N″ wherein P is a hydroxy protecting group, e.g., tertiary butyldimethylsilyl, by reaction in an inert organic solvent, e.g., methylene chloride, with O-2naphthalenylcarbonochloridothioate at room temperature until the reaction is completed in about one hour. The product, compound N″ is then recovered in high yield.

Compound N′ wherein P is hydrogen can also be made from anhydropenicillin, compound 1, through its hydroxy protected analog, compound 2, by converting compound 2 into a dithiobisazetidinone as illustrated in the following Reaction Scheme C.

REACTION SCHEME C

Reaction Scheme C
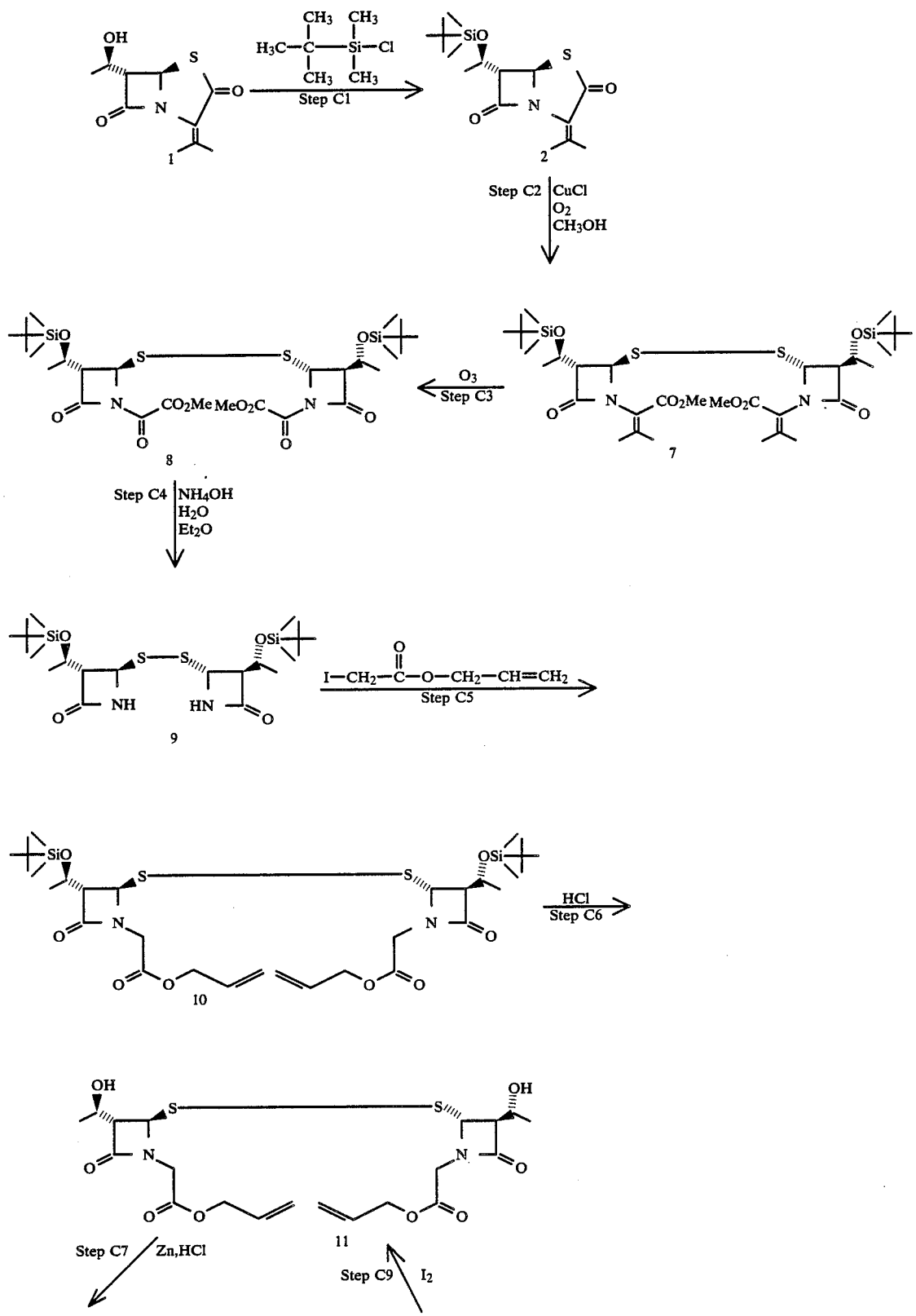

-continued
Reaction Scheme C

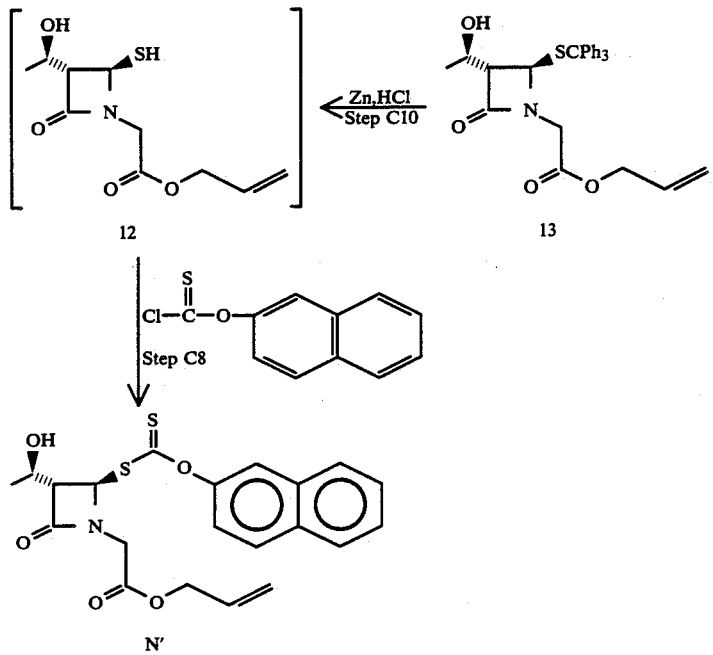

Step C1 of Reaction Scheme C is identical to Step A1 of Reaction Scheme A.

In Step C2, compound 2 is converted to Compound 7 by reaction with oxygen and a copper salt, e.g. cupric acetate, cupric chloride and cuprous chloride, cuprous chloride is preferred, in a lower alkanol, preferably methanol. The reaction takes about one day at moderately elevated temperatures, e g., about 40° C. to 60° C., preferably about 50° C. The product, compound 7, is recovered as a white solid.

In Step C3, compound 7 is converted to compound 8 by treatment with ozone in an inert organic solvent, e.g. methylene chloride, at cold temperatures, e.g. about −78° C. until a blue color is maintained, then treatment with dimethyl sulfide at room temperature. The resulting product, compound 8, is recovered as a white solid In Step C4, the nitrogen of compound 8 is deprotected by reaction in an inert organic solvent, e.g. ethyl ether, with aqueous ammonium hydroxide at about −10° C. to +10° C. preferably 0° C., the product, compound 9, is recovered as a white solid.

In Step C5, the nitrogen of compound 9 is reacted with a halomethylallyloxycarbonyl, preferably allyliodoacetate, by reaction in an anhydrous inert organic solvent, e.g. tetrahydrofuran (THF), and an inorganic base such as sodium hydride or potassium carbonate, preferably sodium hydride, at cold temperatures of about 20° C. to −40° C., preferably −30° C. for about one day. The product, compound 10, is recovered as a viscous oil. Other carboxy protecting groups can be used in place of allyl by replacing the halomethylallyloxycarbonyl reactant with appropriately protected halomethyl carboxylic acids, a typical suitable protecting moiety is paranitrobenzyl. Other protecting groups, particularly those which are readily removable and compatible with the reactants and products are known in the art.

In Step C6, the hydroxy of compound 10 is deprotected by reaction in an inert organic solvent, e.g. THF, with hydrochloric acid at room temperature until the reaction is complete as evidenced by thin layer chromatography (tlc), resulting in compound 11 which is used in the next step without isolation.

In Step C7, the disulfide bond of compound 11 is reduced by reaction with zinc and hydrochloric acid at room temperature until the reaction is completed as evidenced by tlc. Compound 12 is produced and is used in the next step without purification. Steps C6 and C7 are carried out successively in one pot.

In Step C8, compound N' wherein P is hydrogen, is made from compound 12 by reaction of compound 12 with O-2-naphthalenylcarbonochloridothioate in an inert organic solvent, e.g. methylene chloride, with or without an organic nitrogen containing base, e.g., pyridine, anilines or lower alkyl amines, with triethylamine preferred, at about 0° C. under an inert atmosphere, e.g. nitrogen, for about one hour. The product, compound N, is recovered as a white solid.

Compound 11 can also be made from compound 13 as shown in Reaction Scheme C, Step C9 by reaction with iodine in an anhydrous inert organic solvent, e.g. toluene, at about 0° C. The product, compound 11, is produced and need not be recovered for use in the next step.

In Step C10, compound 13 is converted to compound 12 by reaction with zinc and methanolic hydrochloric acid in an inert organic solvent, e.g. THF, under an inert atmosphere, e.g. nitrogen, at about 0° C. until the reaction is complete as evidence by tlc. The resulting product, compound 12, can be converted to compound N' without purification.

Compound 13 is a known compound and can be prepared from the disclosures of U.S Pat. Nos. 4,503,064; 4,530,793 and 4,559,333.

As used herein "hydroxy protecting group" means any group conventionally used for this purpose, with the only requirements being compatibility during protection and deprotection reactions with conventional reagents for this purpose which will not adversely affect the structure of the compounds. Typical of such groups are those listed in Green, "Protecting Groups in Organic Synthesis" John Wiley and Sons, New York, N.Y. (1981), e.g., ethers such as methyl, methoxymethyl, methylthiomethyl, 2-methoxyethoxymethyl, bis(2-chlorethoxy)methyl, tetrahydropyranyl, tetrahydrothiopyranyl, 4-methoxytetrahydropyranyl, 4-methoxytetrahydrothiopyranyl, tetrahydrofuranyl, tetrahydrothiofuranyl, 1-ethoxyethyl, 1-methyl-1-methoxyethyl, 2-(phenylselenyl)ethyl, t-butyl, allyl, benzyl, o-nitrobenzyl, triphenylmethyl, alpha naphthyl diphenylmethyl, para methoxyphenyldiphenylmethyl, 9-(9-phenyl-10-oxo)anthryl, trimethylsilyl, isoamyldimethylsilyl, isopropyldimethylsilyl, t-butyldimethylsilyl, t-butyldiphenylsilyl, tribenzylsilyl, and triisopropylsilyl, as well as esters such as formate, acetate, trichloroacetate, phenoxyacetate, isobutyrate, pivaloate, adamantoate, benzoate, 2,4,5-trimethylbenzoate, methyl carbonate, 2,2,2-trichloroethyl carbonate, allyl carbonate, paranitrophenyl carbonate, benzyl carbonate, paranitrobenzyl carbonate, S-benzyl thiocarbonate, N-phenylcarbonate, nitrate, 2,4-dinitrophenylsulfenate and the like. Most preferred for use in this invention are tertiarybutyldimethylsilyl ether. Others which are very suitable for use in this invention are 2,2,2-trichloroethoxycarbonyl ester, acetate ester, 1-ethoxyethyl ether and isoamyldimethylsilyl ether.

"Carboxy protecting group" means conventional carboxy protectors such as allyl, p-nitrobenzyl, benzyl or benzyhydryl, with allyl preferred.

"Readily removable" means the group can be removed easily by relatively mild reaction conditions without adversely affecting the substrate.

A "suitable inert organic solvent" means any organic solvent or combination of solvents that is unreactive in the reaction being conducted and is a solvent for the reactants. Such solvents used in the various reactions of this invention are identified in the discussion of the reaction schemes and in the examples. Typical suitable solvents are halogenated compounds such as chloroform or methylene chloride; heterocyclic compounds such as tetrahydrofuran (THF); dimethylformamide; mono or biphasic mixed or buffered solvents such as lower alkanols ($C_1$-$C_6$ branched or straight chain alkanols) and ether or ammonium acetate dissolved in water, e.g., methanol and ammonium acetate dissolved in water, methanol and ether; lower alkanols such as methanol; lower alkyl carboxylic acids ($C_2$-$C_6$ straight or branched chain alkyl carboxylic acids) such as acetic acid.

"Mineral acid" means inorganic acids such as hydrochloric acid, nitric acid, sulfuric acid and phosphoric acid.

The following examples describe the process of the present invention. Throughout these examples "NMR" denotes nuclear magnetic resonance spectra, the spectra described, although in some cases incomplete, are sufficient to identify the compound involved; "mp" means melting point; "HPLC" means high pressure liquid chromatography; "ether" means diethylether; and the boiling range of the petroleum ether (pet ether) is 35° C.—60° C. Chromatograph refers to flash chromatography on silica gel following the procedure of Still, et al., *J. Organ. Chem.*, 43, 2923 (1978).

EXAMPLE 1

(5R,6S,8R)-6-[1-(t-Butyldimethylsilyloxy)ethyl]-3,7-dioxo-4-thia-1-azabicyclo[3.2.0]heptane Take 2.019 grams (0.0059 moles) (5R,6S,8R)-6-[1-(t-butyldimethylsilyloxy)ethyl]-3,7-dioxo-2-(1-methylethylidene)-4-thia-1-azabicyclo-[3.2.0.]heptane, 25 ml dry acetone and add to a nitrogen-flushed 100 ml 3necked flask. Cool to about −78° C., bubble ozone through until the solution remains a blue color and stir for 5 minutes, then bubble nitrogen through until the solution is colorless yielding (5R,6S,8R)-6-[1-(t-butyldimethylsilyloxy)ethyl]-4-thia-2,3,7-trioxo-1-azabicyclo [3.2.0]heptane which is not isolated during the reaction but is identified based on its $^{13}C$ NMR spectra.

$^{13}C$ NMR: ($CD_3COCD_3$, BB), δ=189.8, 164.2, 156.9, 69.8, 65.0, 50.4, 25.9, 21.7, 18.4, −4.0, −5.5.

Add 3.44 grams (0.0207 moles) freshly distilled triethylphosphite and let warm slowly to room temperature. Add 0.5 ml water after 4 hours, stir for 30 minutes and concentrate using a rotary evaporator. Flash chromatograph the residue on silica gel (5–100% ethyl ether/pet ether) to yield the title product as a white solid.

mp: 65°–66° C. (Recrystallized from ethyl ether/pet ether).

$^1H$ NMR: ($CDCl_3$), δ=5.37 (s,1H), 4.37 (d,1H,J=16.8 Hz), 4.30 (m,1H), 3.53 (dd,1H,J=1.5,4.4 Hz), 3.44 (dd,1H,J=0.9,16.8 Hz), 1.27 (d,3H,J=6.2 Hz), 0.87 (s,9H), 0.08 (s,3H) 0.07 (s,3H).

EXAMPLE 2

(3S,4R,5R)-1-(Allyloxycarbonyl)methyl-3-[1-(t-butyldimethylsilyloxy)ethyl]4-8-naphthoxythiocarbonylthio-2-azetidinone Take 0.317 grams (0.0011 moles) (5R,6S,8R)-6-[1-(t-butyldimethylsilyloxy)ethyl]-3,7-dioxo-4-thia-1-azabicyclo[3.2.0]heptane, 0.063 grams (0.0011 moles) allyl alcohol, 10 ml acetonitrile and add to a nitrogen-flushed 25 ml flask. Then add silver imidazolate (0.187 grams, 0.0011 moles), the flask protected from light with aluminum foil and the reaction mixture stirred at RT for 24 hours. Add another equivalent of allyl alcohol (0.063 grams, 0.0011 moles). After another 24 hours, add 25 ml methylene chloride, 25 ml brine and 10 ml water, separate the layers, extract the aqueous layer with 1×25 ml methylene chloride, dry the combined organic layers with $Na_2SO_4$ and concentrate using a rotary evaporator. Dissolve the crude solid in 20 ml methylene chloride, cool to 0° C., add 0.623 grams (0.0012 moles) O-2naphthalenylcarbonochloridothioate and stir the reaction mixture for 24 hours. Remove the solid formed by filtering through a pad of celite, wash the celite pad with 3×25 ml portions methylene chloride, then wash the combined organic layers with 1×25 ml 5% HCl, 1×25 ml $H_2O$, 1×25 ml saturated $NaHCO_3$, 1×25 ml brine and dry ($MgSO_4$). Flash chromatograph on silica gel (50% ethyl ether/pet ether) the residue obtained after concentration using a rotary evaporator to yield the product.

$^1H$ NMR: ($CDCl_3$), δ=8.00–7.25 (br m,7H), 5.89 (d,1H,J=2.6 Hz), 4.28 (d,1H,J=17.8 Hz), 3.96 (d,1H,J=17.8 Hz), 3.37 (dd,1H,J=2.5,6.0 Hz), 1.34 (d,3H,J=6.1 Hz), 0.91 (s,9H), 0.12 (s,6H).

EXAMPLE 3

(3S,4R,5R)-1-(Allyloxycarbonyl)methyl-3-(1-hydroxyethyl)-4-β-naphthoxythiocarbonylthio-2-azetidinone Take 0.290 grams (0.0010 moles) (5R,6S,8R)-6-[1-(t-butyldimethylsilyloxy)ethyl]-3,7-dioxo-4-thia-1-azabicyclo[3.2.0]heptane, 3 ml allyl alcohol, 2 pipette drops concentrated HCl and add to a nitrogen-flushed 25 ml flask. After 30 hours stirring at room temperature, concentrate on a rotary evaporator, dissolve the residue in 10 ml methylene chloride, cool to 0° C. and add 0.250 grams (0.0011 moles) O-2-naphthalenylcarbonochloridothioate. After 1 hour stirring at room temperature add 50 ml ethyl ether, 10 ml H$_2$O, separate, extract the aqueous layer with 1×25 ml ethyl ether, wash the combined organic layers with 2×20 ml 5% HCl, 1×20 ml brine, 1×20 ml saturated NaHCO$_3$, 1×20 ml brine and dry (MgSO$_4$). Concentrate using a rotary evaporator and flash chromatograph the residue on silica gel (15–100% ethyl ether/pet ether) to yield the product.

$^1$H NMR: (CDCl$_3$), δ=7.93–7.21 (br m, 7H), 5.96 (d,1H,J=2.5 Hz), 5.82 (m,1H), 4.37 (d,1H,J=18.1 Hz), 3.92 (d,1H,J=18.1 Hz), 3.47 (dd,1H,J=2.5,5.4 Hz), 2.25 (d,1H,J=4.2 Hz), 1.41 (d,3H,J=6.4 Hz).

EXAMPLE 4

(3S,4R,5R,3′S,4′R,5′R)-4,4′-Dithiobis-3-[1-t-butyldimethylsilyloxy)ethyl]-1-(1-methoxycarbonyl-2-methyl-1-propenyl)-2-azetidinone Take 25.1 grams (0.0735 moles) (5R,6S,8R)-6-[1-(t-butyldimethylsilyloxy)ethyl]-3,7-dioxo-2-(1-methylethylidene)-4-thia-1-azabicyclo[3.2.0]heptane, 500 ml methanol and add to a 1-L flask. Bubble oxygen through for 5 minutes, place the flask in an oil bath at 0° C. and add 4.05 grams (0.0412 moles) cuprous chloride. After 3 hours bubble more oxygen through. Remove the oil bath after 22.5 hours, cool (ice bath) the reaction mixture, add 500 ml ethyl ether, 100 ml 5% HCl and filter the solution through a pad of celite. Wash the organic layer with 1×100 ml brine, 2×100 ml saturated NaHCO$_3$, 1×150 ml brine, dry (MgSO$_4$) and concentrate using a rotary evaporator. Recrystallization of the residue (EtOH) yields the product as a white solid.

mp: 124°–125° C. (recrystallized from EtOH).

$^1$H NMR: (CDCl$_3$δ=5.14 (d,2H,J=2.2 Hz), 4.26 (m,2H), 3.72 (s,6H), 3.40 (dd,2H,J=2.2,6.1 Hz), 2.21 (s,6H), 1.94 (s,6H), 1.33 (d,6H,J=6.3 Hz), 0.88 (s,18H), 0.09 (s,6H), 0.07 (s,6H).

A second, minor product is present in the mother liquors and was isolated and identified as (3S,4R,5R,3′S,4′R,5′R)-4,4′-trithiobis-3-[1-(t-butyldimethylsilyloxy)ethyl]-1-(1-methoxycarbonyl-2-methyl-1-propenyl)-2-azetidinone.

$^1$H NMR: (CDCl$_3$), δ=5.4 (d,2H,J=2.5 Hz), 4.29 (m,2H), 3.74 (s,6H), 3.29 (dd,2H,J=2.5,3.9 Hz), 2.23 (s,6H), 1.94 (s,6H), 1.23 (d,6H,J=6.3 Hz), 0.85 (s,18H), 0.07 (s,6H), 0.04 (s,6H).

Add to a 250 ml flask the mother liquors from the recrystallization (8.20 grams, approximately a 2:1 ratio of (3S,4R,5R,3′S,4′R,5′R)-4,4′-trithiobis-3-[1-(t-butyldimethylsilyloxy)ethyl]-1-(1-methoxycarbonyl-2-methyl-1-propenyl)-2-azetidinone and (3S,4R,5R,3′S,4′R,5′R)-4,4′-dithiobis-3-[1-(t-butyldimethylsilyloxy)ethyl]-1-(1-methoxycarbonyl-2-methyl-1-propenyl)-2-azetidinone), 1.90 grams (0.0072 moles) triphenylphosphine and 50 ml acetonitrile. Stir for 3 hours, then add 40 ml ethyl ether, filter off the white solid and concentrate the filtrate using a rotary evaporator. Flash chromatograph the crude product on silica gel (25–70% ethyl ether/pet ether) to yield additional (3S,4R,5R,3′S,4′R,5′R)-4,4′-dithiobis-3-[1-(t-butyldimethylsilyloxy)ethyl]-1-(1-methoxycarbonyl-2-methyl-1-propenyl)-2-azetidinone as a white solid.

EXAMPLE 5

(3S,4R,5R,3′S,4′R,5′R)-4,4′-Dithiobis-3-[1-(t-butyldimethylsilyloxy)ethyl]-1-(methoxycarbonyl)carbonyl-2-azetidinone Take 10.07 grams (0.0135 moles) (3S,4R,5R,3′S,4′R,5′R)-4,4′-dithiobis-3-[1-(t-butyldimethylsilyloxy)ethyl]-1-(1-methoxycarbonyl-2-methyl-1-propenyl)-2-azetidinone, 60 ml methylene chloride and place in a 500 ml flask. Cool to −78° C. (dry ice-acetone bath), bubble ozone through until the solution remains a blue color, stir 5 minutes, bubble nitrogen through until the solution is colorless, add 3.38 grams (0.0544 moles) dimethylsulfide and allow to warm to room temperature. After 3 hours concentrate the reaction mixture using a rotary evaporator to give a white solid. Dissolve the solid in 300 ml ethyl ether, wash with 1×50 ml brine, dry (MgSO$_4$) and concentrate using a rotary evaporator. Recrystallize (ethyl ether/pet ether) the crude product to yield pure product as a white solid.

mp: 147.5°–148.5° C. (recrystallized from ethyl ether/pet ether).

$^1$H NMR: (CDCl$_3$), δ=5.37 (d,2H,J=2.8 Hz), 4.36 (m,2H), 3.91 (s,6H), 3.62 (t,2H,J=2.8 Hz), 1.25 (d,6H,J=6.4 Hz), 0.81 (s,18H), 0.06 (s,6H), 0.01 (s,6H).

EXAMPLE 6

(3S,4R,5R,3′S,4′R,5′R)-4,4′-Dithiobis-3-[1-(t-butyldimethylsilyloxy)ethyl]-2-azetidinone Take 10.01 grams (0.0144 moles) (3S,4R,5R,3′S,4′R,5′R)-4,4′-dithiobis-3-[1-(t-butyldimethylsilyloxy)ethyl]-1-(methoxycarbonyl)carbonyl-2-azetidinone, 400 ml ethyl ether and place in a 1-L flask. Cool to 0° C. (ice bath), add 150 ml 5% ammonium hydroxide solution and stir vigorously. After 3 hours, filter off the white precipitate, wash the solid with 400 ml ethyl ether, wash the combined organic layers with 2×100 ml brine, dry (MgSO$_4$) and concentrate using a rotary evaporator. Flash chromatograph the residue on silica gel (50–100% ethyl ether/pet ether) to yield the product as a white solid.

mp: 130.5°–132° C. (recrystallized from ethyl ether/pet ether).

$^1$H NMR: (CDCl$_3$), δ=6.52 (br s, 2H), 4.79 (d,2H,J=2.1 Hz), 4.22 (m,2H), 3.29 (dd,2H,J=2.0,4.4 Hz.), 1.24 (d,6H,J=6.2 Hz), 0.86 (s,18H), 0.064 (s,6H), 0.057 (s,6H).

EXAMPLE 7

(3S,4R,5R,3′S,4′R,5′R)-4,4′-Dithiobis-1-(allyloxycarbonyl)methyl-3-[1-(t-butyldimethylsilyloxy)ethyl]-2-azetidinone Take 2.261 grams (0.0043 moles) (3S,4R,5R,3′S,4′R,5′R)-4,4′-dithiobis-3-[1-(t-butyldimethylsilyloxy)ethyl]-2-azetidinone, 20 ml dry THF, 3.929 grams (0.0174 moles) allyliodoacetate and place in a nitrogen-flushed 250 ml flask. Cool the solution to −30° C. (dry ice-acetone bath), add 0.428 grams (0.0107 moles, 60% oil dispersion) sodium hydride and stir at −30° C. for 24 hours and then 1 hour under reduced pressure (20 torr). Add 200 ml ethyl ether and 50 ml brine, filter off the precipitate formed, wash the organic layer with 2×50 ml brine, dry (MgSO4) and concentrate using a rotary evaporator. Flash chromatograph the residue on silica gel (0–5% ethyl acetate/methylene chloride) to yield the product as a viscous oil.

$^1$H NMR: (CDCl$_3$), δ=5.85 (m,2H), 5.04 (d,2H,J=1.9 Hz), 4.62 (d,4H,J=6.0 Hz), 4.28 (d,2H,J=18.0 Hz), 3.78 (d,2H,J=18.0 Hz), 3.34 (dd,2H,J=1.9,5.1 Hz), 1.27 (d,6H,J=6.4 Hz), 0.86 (s,18H), 0.08 (s,6H), 0.05 (s,6H).

EXAMPLE 8

(3S,4R,5R)-1-(allyloxycarbonyl)methyl-3-(1-hydroxyethyl)-4-sulfhydril-2-azetidinone To a solution of 0.70 g (1.44 mM) of (3S,4R,5R)-1-(allyloxycarbonyl)methyl-3-(1-hdyroxyethyl)-4-triphenylmethylthio-2-azetidinone in 10 ml THF at 0° under N$_2$ atmosphere, add 0.38 g (5.67 mM) of finely powdered zinc. Next, slowly add methanolic HCl [9 ml MeOH/1 ml conc. HCl] until all Zn dissolves. Repeat the steps of Zn followed by methanolic HCl addition until the reduction is complete as judged by tlc. Add 100 ml cold (0°) CH$_2$Cl$_2$ followed by ice and 5 ml sat. aq. NaCl. Separate the aqueous layer, re-extract the aqueous layer with CH$_2$Cl$_2$, combine the organic phases and wash with cold (0° C.) sat. aq. NaCl soln. until the washes are neutral. Dry organic layer over anhyd. MgSO$_4$ and concentrate in vacuo to give a white solid as a mixture of title compound and triphenylmethane suitable for further reaction without purification.

NMR (CDCl$_3$): δ 1.35 (d,3H,J=7 Hz), 2.15 (d,1H,J=10 Hz), 2.6 (br,1H), 3.17 (d of d,1H,J=2 Hz and 6Hz), 3.77 and 4.2 (2d,2H,J=18 Hz), 4.3 (m,1H), 4.6 (d,2H,J=7 Hz), 5.05 (d of d,1H,J=2 Hz and 10 Hz), 5.35 (m,2H), 5.95 (m,1H).

EXAMPLE 9

(3S,4R,5R,3'S,4'R,5'R)-4,4'-Dithiobis-1-(allyloxycarbonyl)methyl-3-(1-hydroxyethyl)-2-azetidinone To a solution of 0.125 g (0.256 mM) of (3S,4R,5R)-1-(allyloxycarbonyl)methyl-3-[1-hydroxyethyl]-4-triphenylmethylthio-2-azetidinone in 5 ml dry toluene at 0° C., add 0.033 g (0.256 mM) I$_2$. Stir the reaction mixture for 2 hr at 0° C., dilute with CH$_2$Cl$_2$, wash with 1:1 mixture of sat. aq. NaCl/H$_2$O containing traces of Na$_2$S$_2$O$_3$ followed by distilled water, dry the organic layer over anhyd. Na$_2$SO$_4$ and concentrate in vacuo to give a white solid as a mixture of the title compound and triphenylmethylcarbinol[1], suitable for further reaction without purification.

[1]: Use of an alcohol, e.g. methanol, leads to ether, e.g. triphenylmethyl ether as a by product.

NMR (CDCl$_3$): δ 1.38 (d,6H,J=7.5 Hz), 2.84 (br,2H), 3.4 (d of d,2H,J=3.5 Hz and 7 Hz), 3.8 and 4.3 (2d,4H,J=18 Hz), 4.25 (m,2H), 4.65 (d,4H,J=7.5 Hz), 5.05 (d,2H,J=3 Hz), 5.3 (m,4H), 5.87 (m,2H).

EXAMPLE 10

(3S,4R,5R)-1-(allyloxycarbonyl)methyl-3-(1-hydroxyethyl)-4-sulfhydril-2-azetidinone To a stirred solution of 0.89 g (0.88 mM) of a mixture of (3S,4R,5R,3'S,4'R,5'R)-4,4'-dithiobis-1-(allyloxycarbonyl)methyl-3-(1-hydroxyethyl)-2-azetidinone and triphenylcarbinol in 10 ml THF containing 1 ml conc. HCl at 0° C. under N$_2$ atmosphere, slowly add finely powdered zinc over a 1 hr period until the disulfide reduction is complete. Stir the reaction mixture for an additional 0.5 hr, dilute with 60 ml diethyl ether and wash with distilled water until the washes are neutral. Dry the ether layer with anhydrous Na$_2$SO$_4$ and concentrate in vacuo to obtain a white solid as a mixture of the title compound and triphenylcarbinol, suitable for further reaction without purification.

NMR: Identical to the NMR for the compound produced in Example 8.

EXAMPLE 11

(3S,4R,5R)-1-(allyloxycarbonyl)methyl-3-(1-hydroxyethyl)-4-sulfhydril-2-azetidinone To a solution of 0.43 g (0.6 mM) of (3S,4R,5R,3'S,4'R,5'R)-4,4'-dithiobis-1-(allyloxycarbonyl)methyl-3-[1-(t-butyldimethylsilyloxy)ethyl]-2-azetidinone in 10 ml THF at room temperature add 1.5 ml of 10N aq. HCl and stir the reaction mixture until desilylation is complete (2–4 hr) as judged by tlc. To this stirred solution of desilylated disulfide slowly add finely powdered Zn in small portions over 4 Hr until the disulfide reduction is complete as judged by tlc. Dilute this reaction mixture with 100 ml ethyl acetate and wash with saturated aq. NaCl solution until the washes are neutral. Dry the organic phase over anhyd. Na$_2$SO$_4$ and concentrate in vacuo at or below room temperature to obtain an oil consisting of the title compound and t-butyldimethylsilyl by products, suitable for further reaction without any purification.

NMR: Identical to the NMR for the compound produced in Example 8.

EXAMPLE 12

(3S,4R,5R)-1-(allyloxycarbonyl)methyl-3-(1-hydroxyethyl)-4-8-naphthoxythiocarbonylthio-2-azetidinone To a solution of 0.65 g (1.34 mM) of a mixture of (3S,4R,5R)-1-(allyloxycarbonyl)methyl-3-(1-hydroxyethyl)-4-sulfhydril-2-azetidinone and triphenylmethane[1] in 18 ml CH$_2$Cl$_2$ at 0° C. under N$_2$ atmosphere add 0.32 g (1.44 mM) O-2-naphthalenyl- carbonochloridothioate (NCCT) followed by 0.2 ml (1.44 mM) dry triethylamine. Stir the reaction mixture for 50 min. at 0° C., dilute with CH$_2$Cl$_2$ and wash with distilled water followed by a 1:1 mixture of aq. sat. NaCl:distilled water. Separate the organic phase, dry over anhydrous MgSO$_4$ and concentrate in vacuo to give an off white solid. Chromatograph this solid (silica gel; CH$_2$Cl$_2$ followed by EtOAc/CH$_2$Cl$_2$ (1:19) to obtain the title compound as a white solid, mp 76°–78° C.

[1]: The presence of triphenylcarbinol, triphenylmethyl ether, or t-butyldimethylsilyl by products in place of triphenylmethane does not alter the quality of the product.

NMR (CDCl$_3$): δ 1.42 (d,3H,J=7 Hz), 2.25 (br,1H), 3.4 (d of d,1H,J=3 Hz and 6 Hz), 3.85 and 4.37 (J=18 Hz), 4.2–4.6 (m,3H), 5.17 (m,2H), 5.75 (m,1H), 5.9 (d,1H,J=2 Hz), 7.1 to 7.9 (m,7H).

We claim:

1. A compound represented by the formula

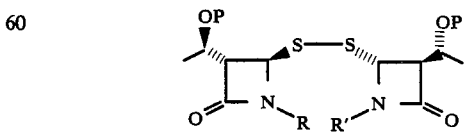

wherein each P is hydrogen or a hydroxy protecting group and R and R' are each the same and are hydrogen,

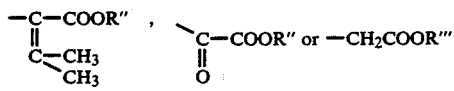
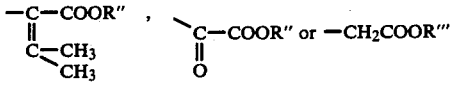
wherein R″ is lower alkyl and R‴ is a carboxy protecting group.
2. A compound of claim 1 wherein R″ is methyl.
3. A compound of claim 1 wherein R‴ is allyl.
* * * * *

UNITED STATES PATENT AND TRADEMARK OFFICE
CERTIFICATE OF CORRECTION

PATENT NO. : 4,948,885

DATED : August 14, 1990

INVENTOR(S) : Donald Hou, Et al.

It is certified that error appears in the above-identified patent and that said Letters Patent is hereby corrected as shown below:

On the cover sheet, the Assignee should read Schering Corporation, Kenilworth, N.J.

Signed and Sealed this

Tenth Day of March, 1992

Attest:

HARRY F. MANBECK, JR.

*Attesting Officer*  *Commissioner of Patents and Trademarks*